(12) United States Patent
Jetti et al.

(10) Patent No.: US 10,087,193 B2
(45) Date of Patent: Oct. 2, 2018

(54) CRYSTALLINE FORMS OF DOLUTEGRAVIR SODIUM

(71) Applicant: Mylan Laboratories Ltd., Maharashtra (IN)

(72) Inventors: Ramakoteswara Rao Jetti, Maharashtra (IN); Satish Beeravelly, Maharashtra (IN); Madhu Murthy Nadella, Maharashtra (IN); Haribabu Nandipati, Maharashtra (IN)

(73) Assignee: Mylan Laboratories Limited (IN)

( * ) Notice: Subject to any disclaimer, the term of this patent is extended or adjusted under 35 U.S.C. 154(b) by 0 days.

(21) Appl. No.: 15/114,991

(22) PCT Filed: Feb. 4, 2015

(86) PCT No.: PCT/IB2015/050841
§ 371 (c)(1),
(2) Date: Jul. 28, 2016

(87) PCT Pub. No.: WO2015/118460
PCT Pub. Date: Aug. 13, 2015

(65) Prior Publication Data
US 2016/0347766 A1 Dec. 1, 2016

(30) Foreign Application Priority Data
Feb. 7, 2014 (IN) .......................... 455/MUM/2014

(51) Int. Cl.
*C07D 498/14* (2006.01)

(52) U.S. Cl.
CPC ........ *C07D 498/14* (2013.01); *C07B 2200/13* (2013.01)

(58) Field of Classification Search
CPC .................................................... C07D 498/14
USPC ........................................................... 544/95
See application file for complete search history.

(56) References Cited

FOREIGN PATENT DOCUMENTS

| | | |
|---|---|---|
| WO | 2010/068253 | 6/2010 |
| WO | 2013/038407 | 3/2013 |
| WO | 2015/009927 | 1/2015 |
| WO | 2015/019310 | 2/2015 |

OTHER PUBLICATIONS

International Search Report for corresponding International Patent Application No. PCT/IB2015/50841 dated Jun. 5, 2015.
Written Opinion of the International Search Authority for corresponding International Patent Application No. PCT/IB2015/50841 dated Feb. 12, 2010.

*Primary Examiner* — Kahsay Habte

(57) ABSTRACT

The present disclosure relates to novel crystalline dolutegravir sodium Form-M2, Form-M3, Form-M4 and process for the preparation thereof.

15 Claims, 3 Drawing Sheets

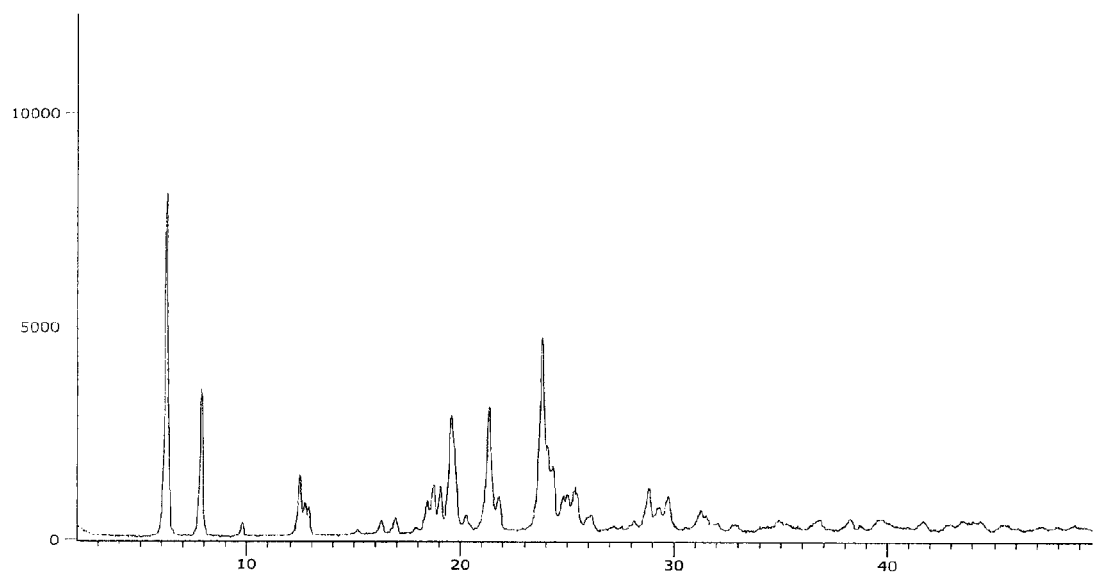
Figure 1. Powder X-ray diffraction pattern of crystalline dolutegravir sodium Form-M2

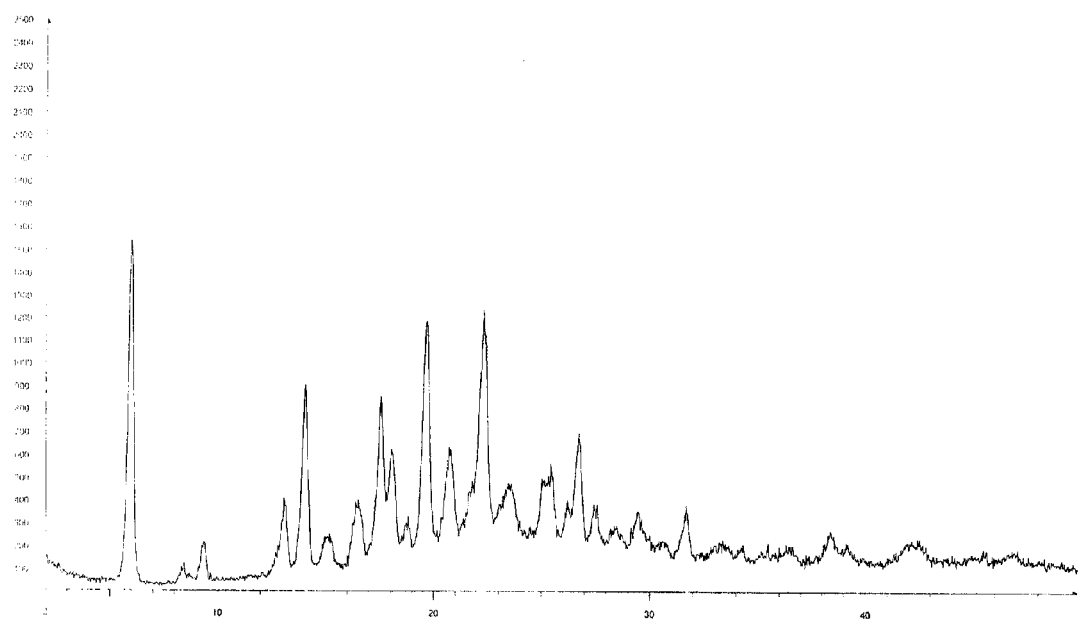
Figure 2. Powder X-ray diffraction pattern of crystalline dolutegravir sodium Form-M3

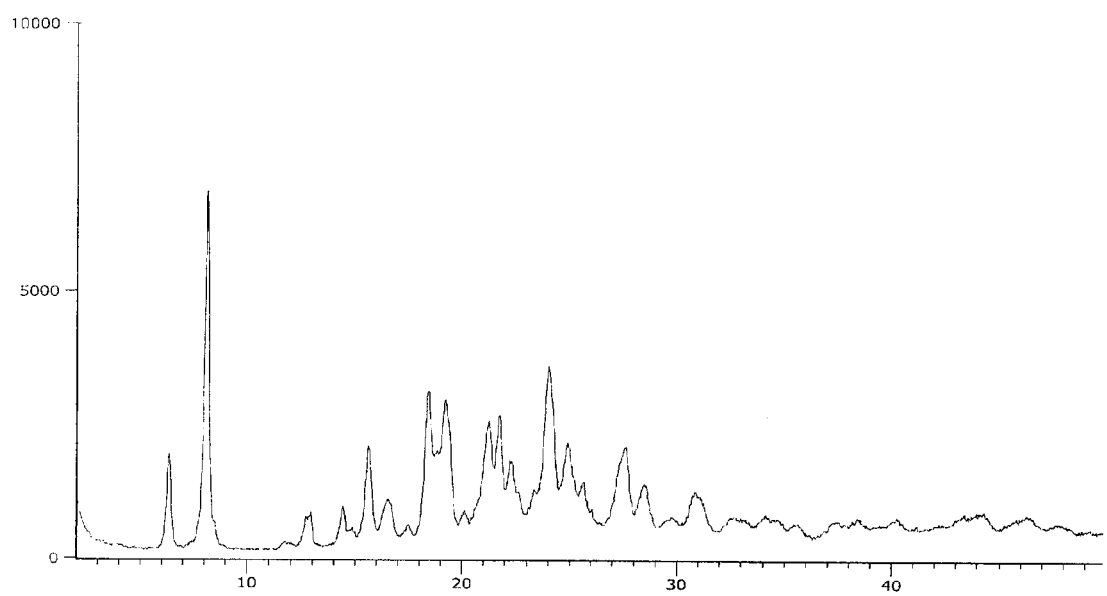
Figure 3. Powder X-ray diffraction pattern of crystalline dolutegravir sodium Form-M4

CRYSTALLINE FORMS OF DOLUTEGRAVIR SODIUM

CROSS-REFERENCE TO RELATED APPLICATIONS

This application is a national stage filing of PCT application no. PCT/IB2015/050841, filed Feb. 4, 2015, which in turn claimed priority to and the benefit of priority to 455/MUM/2014, filed on Feb. 7, 2014.

BACKGROUND OF THE INVENTION

Field of the Disclosure

The present disclosure relates to novel crystalline forms of dolutegravir sodium and a process for the preparation thereof.

Description of the Related Art

Dolutegravir (DTG, GSK1349572) is an integrase inhibitor being developed for the treatment of human immunodeficiency virus (HIV)-1 infection.

TIVICAY® tablets contain dolutegravir sodium, which is an HIV-1 integrase strand transfer inhibitor (INSTI). Dolutegravir sodium is chemically known as sodium (4R, 12aS)-9-((2,4-difluorobenzyl)carbamoyl)-4-methyl-6, 8-dioxo-3, 4, 6, 8, 12, 12a-hexahydro-2H-pyrido[1',2':4,5]pyrazino[2, 1-b][1,3]oxazin-7-olate, having the structure below:

Formula-I

PCT Publication No. WO2010068253A1 (which is hereby incorporated by reference) discloses a crystalline form of dolutegravir sodium characterized by the following powder X-ray diffraction (PXRD) pattern having peaks at 6.4, 9.2, 13.8, 19.2 and 21.8±0.2° 2θ; and a crystalline form of dolutegravir sodium hydrate characterized by the following diffraction peaks in the PXRD pattern at 8.0, 9.3, 11.3, 16.0 and 22.8±0.2° 2θ.

PCT Publication No. WO2013038407A1 (which is hereby incorporated by reference) discloses amorphous dolutegravir sodium characterized by the following characteristic peaks in infrared absorption spectrum at about 662±4, 766±4, 851±4, 886±4, 959±4, 1025±4, 1055±4, 1090±4, 1133±4, 1206±4, 1233±4, 1248±4, 1279±4, 1318±4, 1356±4, 2325±4 and 2348±4 cm$^{-1}$.

The present disclosure provides novel crystalline forms of dolutegravir sodium.

SUMMARY OF THE DISCLOSURE

A first aspect of the present disclosure provides crystalline dolutegravir sodium Form-M2 which may be characterized by the PXRD pattern shown in FIG. 1.

Another aspect of the present disclosure provides a process for the preparation of crystalline dolutegravir sodium Form-M2 by the following steps:
a) dissolving dolutegravir in an organic solvent at elevated temperature;
b) adding alcoholic sodium hydroxide solution; and
c) isolating crystalline dolutegravir sodium Form-M2.

Yet another aspect of the present disclosure provides crystalline dolutegravir sodium Form-M3 which may be characterized by the PXRD pattern shown in FIG. 2.

Another aspect of the present disclosure provides a process for the preparation of crystalline dolutegravir sodium Form-M3 by drying dolutegravir sodium Form-M2 under reduced pressure at 75-85° C. for 12-15 hours.

Another aspect of the present disclosure is to provide crystalline dolutegravir sodium Form-M4 which may be characterized by the PXRD pattern shown in FIG. 3.

Another aspect of the present disclosure provides a process for the preparation of crystalline dolutegravir sodium Form-M4 by drying dolutegravir sodium Form-M3 or Form-M2 under reduced pressure at 70-140° C. for 15-48 hours or drying dolutegravir sodium Form-M3 or Form M2 at 190-210° C. for 15-20 minutes.

BRIEF DESCRIPTION OF THE DRAWINGS

Further aspects of the present disclosure together with additional features contributing thereto and advantages accruing there from will be apparent from the following description of embodiments of the disclosure, which are shown in the accompanying drawing figures wherein:

FIG. 1 is an X-ray powder diffractogram of crystalline dolutegravir sodium Form-M2;

FIG. 2 is an X-ray powder diffractogram of crystalline dolutegravir sodium Form-M3; and FIG. 3 is an X-ray powder diffractogram of crystalline dolutegravir sodium Form-M4.

DETAILED DESCRIPTION OF THE DISCLOSURE

It is to be understood that the description of the present invention has been simplified to illustrate elements that are relevant for a clear understanding of the invention, while eliminating, for purposes of clarity, other elements that may be well known.

The present invention encompasses novel crystalline forms of dolutegravir sodium Form-M2, Form-M3, and Form-M4, as well as processes for their preparation.

The polymorphs of the present invention may be characterized by a PXRD pattern. Thus, the PXRD patterns of the polymorphs of the disclosure were measured on BRUKER D-8 Discover powder diffractometer equipped with goniometer of θ/2θ configuration and Lynx Eye detector. The Cu-anode X-ray tube was operated at 40 kV and 30 mA. The experiments were conducted over the 2θ range of 2.0°-50.0°, 0.030° step size and 0.4 seconds step time.

One aspect of the present disclosure provides crystalline dolutegravir sodium Form-M2, characterized by a PXRD pattern that contains significant peaks at 2θ angles at about 6.23, 7.87, 19.54, 21.34 and 23.84±0.2°.

According to the present disclosure, crystalline dolutegravir sodium Form-M2 may be further characterized by an PXRD pattern that contains significant peaks at 2θ angles at about 6.23, 7.87, 9.80, 12.46, 12.69, 12.88, 15.15, 16.28, 16.94, 17.91, 18.42, 18.74, 19.06, 19.54, 19.75, 20.25, 21.34, 21.82, 23.84, 24.36, 24.81, 25.02, 25.32, 25.51, 26.17, 27.17, 28.14, 28.82, 29.31, 29.75, 31.25, 31.52, 32.05 and 32.82±0.2°.

Another aspect of the present disclosure provides a process for the preparation of crystalline dolutegravir sodium Form-M2 by the following steps:

a) dissolving dolutegravir in an organic solvent at elevated temperature;
b) adding alcoholic sodium hydroxide solution; and
c) isolating crystalline dolutegravir sodium Form-M2.

According to the present disclosure, dolutegravir is dissolved in an organic solvent at elevated temperature and the solution is filtered through a Hyflo bed to remove undissolved particles. A clear solution of alcoholic sodium hydroxide solution is then added at ambient temperature to produce a solid. The obtained solid may then be filtered and washed with an organic solvent to get crystalline dolutegravir sodium Form-M2.

Within the context of the present disclosure, dolutegravir is dissolved in an organic solvent at an elevated temperature of about 60-85° C. According to the present invention, the dolutegravir starting material may be crystalline or amorphous and may be prepared by a prior-art process well known to those of skill in the art.

Within the context of the present disclosure, the organic solvent may be a polar protic solvent. Examples of suitable polar protic solvents include methanol, ethanol, isopropanol, 1-butanol, 2-butanol, isoamyl alcohol, isobutyl alcohol, 1-pentanol, 1-propanol, 2-prapanol, and mixtures thereof. One of skill in the art will recognize other polar protic solvents that may be employed. After filtering, an alcoholic sodium hydroxide solution may then be added and stirred at ambient temperature. Within the context of the present invention, the alcoholic sodium hydroxide solution may be, as examples, methanolic sodium hydroxide, ethanolic sodium hydroxide, isopropanol sodium hydroxide, or mixtures thereof. In some embodiments of the present invention, it has been found that methanolic sodium hydroxide solution has been particularly useful. It has been found that maintaining a temperature of about 20-35° C. for 3-5 hours is particularly useful for forming a solid.

Yet another aspect of the present invention provides a crystalline dolutegravir sodium Form-M3, characterized by a PXRD pattern that contains significant peaks at 2θ angles at about 5.91, 13.98, 17.51, 19.63 and 22.31±0.2°.

According to the present disclosure, crystalline dolutegravir sodium Form-M3 may be further characterized by an PXRD pattern that contains significant peaks at 2θ angles at about 5.91, 8.38, 9.32, 13.06, 13.98, 15.02, 16.42, 17.51, 18.03, 18.75, 19.63, 20.73, 21.70, 22.31, 23.52, 25.06, 25.45, 26.19, 26.72, 27.51, 29.45, 31.69, 34.28, 38.36 and 45.56±0.2°.

Yet another aspect of the present disclosure provides a process for the preparation of crystalline dolutegravir sodium Form-M3 by drying dolutegravir sodium Form-M2 under reduced pressure at 75-85° C. for 12-15 hours. According to the present disclosure, these drying conditions are critical in the conversion of crystalline dolutegravir sodium Form-M2 to Form-M3.

Yet another aspect of the present disclosure provides crystalline dolutegravir sodium Form-M4, characterized by a PXRD pattern having significant peaks at 2θ angle positions at about 8.10, 18.40, 19.19, 21.23, 21.72 and 24.02±0.2°.

According to the present disclosure, crystalline dolutegravir sodium Form-M4 may be further characterized by a PXRD pattern that contains significant peaks at 2θ angles at about 6.34, 8.10, 11.82, 12.93, 14.43, 15.63, 16.52, 17.46, 18.40, 19.19, 19.41, 20.09, 21.23, 21.72, 22.27, 24.02, 24.90, 25.65, 27.59, 28.44, 29.70, 30.81, 34.11, 35.54, 38.36 and 46.35±0.2°.

Yet another aspect of the present disclosure provides a process for the preparation of crystalline dolutegravir sodium Form-M4 by drying dolutegravir sodium Form-M3 or Form-M2 under reduced pressure at 70-140° C. for 15-48 hours or drying dolutegravir sodium Form-M3 or Form-M2 at 190-210° C. for 15-20 minutes.

In some embodiments of the present invention, it has been found that drying dolutegravir sodium Form-M3 or Form-M2 under vacuum at 120-140° C. for 15-24 hours is particularly effective at producing crystalline dolutegravir sodium Form-M4.

In other embodiments of the present invention, it has been found that drying dolutegravir sodium Form-M3 or Form-M2 at 190-210° C. for 15-20 minutes is particularly effective at producing crystalline dolutegravir sodium Form-M4.

With all of the reactions disclosed above, one of skill in the art will recognize that the reaction conditions (e.g., reaction time or temperature) may be adjusted to achieve appropriate yield without undertaking undue experimentation and without departing from the scope of the present disclosure.

Stability Data

The dolutegravir sodium Form-M2 and Form-M4 prepared according to the present disclosure may have purity of more than 99% when measured by HPLC. Dolutegravir sodium Form-M3 prepared according to the present invention is only metastable and not thermodynamically stable.

The physical and chemical stability of dolutegravir sodium Form-M2 and Form-M4 was determined by storing the samples at 40° C./75% relative humidity (RH) and at 25° C./60% RH for 6 months. At different time points during storage, the crystal structure of the material was analyzed by PXRD, the water content by Karl Fischer, and by HPLC for final purity.

The dolutegravir sodium Form-M2 and Form-M4 show no significant degradation, no substantial increase in moisture content, and no change in PXRD pattern when stored for 6 months at 40° C./75% relative humidity (RH) and at 25° C./60% RH. This indicates that dolutegravir sodium Form-M2 and Form-M4 are physically and chemically stable.

TABLE 1

| Condition\Polymorph | Form-M2 HPLC purity (%) | Form-M2 PXRD | Form-M4 HPLC purity (%) | Form-M4 PXRD |
|---|---|---|---|---|
| at 40° C./75% RH | | | | |
| Initial | 99.7 | Form-M2 | 99.2 | Form-M4 |
| 1 month | 99.6 | Form-M2 | 99.2 | Form-M4 |
| 3 months | 99.5 | Form-M2 | 99.1 | Form-M4 |
| 6 months | 99.5 | Form-M2 | 99.0 | Form-M4 |
| at 25° C./60% RH | | | | |
| Initial | 99.7 | Form-M2 | 99.24 | Form-M4 |
| 1 month | 99.6 | Form-M2 | 99.17 | Form-M4 |
| 3 months | 99.5 | Form-M2 | 99.10 | Form-M4 |
| 6 months | 99.5 | Form-M2 | 99.0 | Form-M4 |

The crystalline dolutegravir sodium Form-M2 or Form-M4 of the present invention may be incorporated into a pharmaceutical formulation for the treatment of HIV in human patients. The pharmaceutical formulation may be an oral dosage form and, in some embodiments, a tablet. The tablet may include such excipients as D-mannitol, microcrystalline cellulose, povidone K29/32, sodium starch glycolate, and sodium stearyl fumarate. The tablet may be coated in a film that may contain the inactive ingredients iron oxide yellow, macrogol/PEG, polyvinyl alcohol-part hydrolyzed, talc, and titanium dioxide. The crystalline dolutegravir sodium Form-M2 or Form-M4 may be administered in conjunction with other active pharmaceutical ingredients, including efavirenz, fosamprenavir, ritonavir, tipranavir, and rifampin.

In view of the above description and the examples below, one of ordinary skill in the art will be able to practice the invention as claimed without undue experimentation. The foregoing will be better understood with reference to the following examples that detail certain procedures for the preparation of molecules, compositions and Formulations according to the present invention. All references made to these examples are for the purposes of illustration. The following examples should not be considered exhaustive, but merely illustrative of only a few of the many aspects and embodiments contemplated by the present disclosure.

EXAMPLES

Example 1

Preparation of Crystalline Dolutegravir Sodium Form-M1

Dolutegravir (200 mg) was dissolved in N-methyl-2-pyrrolidone (6 mL) at 25-30° C. The clear solution was seeded with N-methyl-2-pyrrolidone solvate of dolutegravir sodium Form-M1 (2 mg) and then 0.25 N methanolic sodium hydroxide solution (2 mL) was added and stirred at 25-30° C. for 3-4 hours. The product obtained was filtered and washed with N-methyl-2-pyrrolidone (5 mL) and dried under vacuum at 80° C. for 12-15 hours. The resulting solid was identified as crystalline dolutegravir sodium Form-M1.

Example 2

Preparation of Crystalline Dolutegravir Sodium Form-M2

Dolutegravir (0.5 g) was dissolved in 1-butanol (50 mL) at 70-80° C. to form a clear solution. The clear solution was filtered through a Hyflo bed and washed with 1-butanol (5 mL) at 25-30° C. Methanolic sodium hydroxide solution (5 mL, 0.25 N) was added and stirred at 25-30° C. for 3-5 hours to precipitate the product. The obtained solid was filtered and washed with 1-butanol (5 mL) and identified as crystalline dolutegravir sodium Form-M2.

Example 3

Preparation of Crystalline Dolutegravir Sodium Form-M2

Dolutegravir (0.5 g) was dissolved in a mixture of 1-butanol (15 mL) and methanol (7.5 mL) at 70-80° C. to form a clear solution. The clear solution was filtered through a Hyflo bed and washed with 1-butanol (1 mL) at 25-30° C. Methanolic sodium hydroxide solution (5 mL, 0.25 N) was added and stirred at 25-30° C. for 3-5 hours to precipitate the product. The obtained solid was filtered and washed with 1-butanol (5 mL) at 25-30° C. The resulting solid was identified as crystalline dolutegravir sodium Form-M2.

Example 4

Preparation of Crystalline Dolutegravir Sodium Form-M2

Dolutegravir (5 g) was dissolved in a mixture of 1-butanol (150 mL) and methanol (75 mL) at 70-80° C. to form a clear solution. The clear solution was filtered through a Hyflo bed and washed with 1-butanol (10 mL) at 25-30° C. Methanolic sodium hydroxide solution (5 mL, 0.25 N) was added and stirred at 25-30° C. for 3-5 hours to obtain a solid. The solid was filtered and washed with 1-butanol (5 mL). The resulting solid was identified as crystalline dolutegravir sodium Form-M2.

Example 5

Preparation of Crystalline Dolutegravir Sodium Form-M2

Dolutegravir (3 g) was dissolved in 1-butanol (300 mL) at 75-80° C. to form a clear solution. The clear solution was filtered through a Hyflo bed and washed with 1-butanol (6 mL) at 25-30° C. Methanolic sodium hydroxide solution (5 mL, 0.25 N) was added and stirred at 25-30° C. for 3-4 hours to precipitate the product. The obtained solid was filtered, washed with 1-butanol (3 mL), and suction dried at 25-30° C. The resulting solid was identified as crystalline dolutegravir sodium Form-M2.

Example 6

Preparation of Crystalline Dolutegravir Sodium Form-M2

Dolutegravir sodium Form-M1 (2 g) was dissolved in 1-butanol (120 mL) at 75-80° C. to form a clear solution. The clear solution was filtered through a Hyflo bed and washed with 1-butanol (5 mL) at 25-30° C. The clear solution was then stirred at 25-30° C. for 12-15 hours to precipitate the product. The obtained solid was filtered, washed with 1-butanol (5 mL) at 25-30° C. and dried under vacuum at 80° C. for 12-15 hours. The resulting solid was identified as crystalline dolutegravir sodium Form-M2.

Example 7

Preparation of Crystalline Dolutegravir Sodium Form-M3

Dolutegravir sodium Form-M2 obtained as per Example 4 was dried under vacuum at 80° C. for 12-15 hours. The resulting solid was identified as crystalline dolutegravir sodium Form-M3.

Example 8

Preparation of Crystalline Dolutegravir Sodium Form-M4

Dolutegravir sodium Form-M3 obtained as per Example 7 was further dried under vacuum at 80-100° C. for 24-30 hours. The resulting solid was identified as crystalline dolutegravir sodium Form-M4.

Example 9

Preparation of Crystalline Dolutegravir Sodium Form-M4

Dolutegravir sodium (0.2 g) Form-M3 was dried at 200° C. for 15-20 minutes. The resulting solid was identified as crystalline dolutegravir sodium Form-M4.

Example 10

Preparation of Crystalline Dolutegravir Sodium Form-M4

Dolutegravir sodium (1 g) Form-M2 was dried at 200° C. for 15-20 minutes. The resulting solid was identified as crystalline dolutegravir sodium Form-M4.

Example 11

Preparation of Crystalline Dolutegravir Sodium Form-M4

Dolutegravir sodium Form-M2 obtained, as above in Examples 2-6, was further dried under vacuum at 80-100° C. for 24-30 hours. The resulting solid was identified as crystalline dolutegravir sodium Form-M4.

Example 12

Preparation of Crystalline Dolutegravir Sodium Form-M4

Dolutegravir (2.0 kg) was dissolved in a mixture of 1-butanol (1000 L) and methanol (30 L) at 70-80° C. to produce a clear solution. The clear solution was cooled to 50-55° C., filtered through a Hyflo bed at 50-55° C., and washed with 1-butanol (2 L). The clear solution was reheated to 50-55° C. and cooled to 37-40° C. To this, 0.25 N methanolic sodium hydroxide solution (2 L) was added at 37-40° C. The reaction mass was cooled to 25-30° C. and stirred at 25-30° C. for 15-18 hours to precipitate the product. The obtained solid was filtered, washed with 1-butanol (4 L), and dried under vacuum at 100° C. for 16 hours. The sample was then milled and dried at 130° C. under vacuum for 18-24 hours. The resulting solid was identified as crystalline dolutegravir sodium Form-M4.

Example 13

Preparation of Crystalline Dolutegravir Sodium Form-M4

Dolutegravir sodium Form-M2 obtained, as above in Examples 2-6, was further dried at 130° C. under vacuum for 15-24 hours. The resulting solid was identified as crystalline dolutegravir sodium Form-M4.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

We claim:

1. A crystalline dolutegravir sodium Form-M2, which has a powder X-ray diffraction pattern having 2Θ angle of significant peaks at about 6.23, 7.87, 19.54, 21.34 and 23.84 ±0.2°.

2. The crystalline dolutegravir sodium Form-M2 according to claim 1 which has a powder X-ray diffraction pattern having 2Θ angle of significant peaks at about 6.23, 7.87, 9.80, 12.46, 12.69, 12.88, 15.15, 16.28, 16.94, 17.91, 18.42, 18.74, 19.06, 19.54, 19.75, 20.25, 21.34, 21.82, 23.84, 24.36, 24.81, 25.02, 25.32, 25.51, 26.17, 27.17, 28.14, 28.82, 29.31, 29.75, 31.25, 31.52, 32.05 and 32.82±0.2°.

3. A crystalline dolutegravir sodium Form-M2, which has a powder X-ray diffraction pattern as shown in FIG. 1.

4. A process for the preparation of crystalline dolutegravir sodium Form-M2 comprising the steps of:
   a. dissolving dolutegravir in an organic solvent at elevated temperature;
   b. adding alcoholic sodium hydroxide solution; and
   c. isolating crystalline dolutegravir sodium Form-M2.

5. The process of claim 4, wherein organic solvent is a polar protic solvent.

6. The process of claim 5, wherein the polar protic solvent is selected from the group consisting of methanol, ethanol, isopropanol, 1-butanol, 2-butanol, isoamyl alcohol, isobutyl alcohol, 1-pentanol, 1-propanol, 2-prapanol and mixtures thereof and alcoholic sodium hydroxide is selected from methanolic sodium hydroxide, ethanolic sodium hydroxide, isopropanol sodium hydroxide and mixtures thereof.

7. A crystalline dolutegravir sodium Form-M3, which has a powder X-ray diffraction pattern having 2Θ angle of significant peaks at about 5.91, 13.98, 17.51, 19.63 and 22.31 ±0.2°.

8. A crystalline dolutegravir sodium Form-M3, according to claim 7 which has a powder X-ray diffraction pattern having 2Θ angle of significant peaks at about 5.91, 8.38, 9.32, 13.06, 13.98, 15.02, 16.42, 17.51, 18.03, 18.75, 19.63, 20.73, 21.70, 22.31, 23.52, 25.06, 25.45, 26.19, 26.72, 27.51, 29.45, 31.69, 34.28, 38.36 and 45.56±0.2°.

9. A crystalline dolutegravir sodium Form-M3, which has a powder X-ray diffraction pattern as shown in FIG. 2.

10. A process for the preparation of crystalline dolutegravir sodium Form-M3 comprising the step of drying dolutegravir sodium Form-M2 under reduced pressure at a temperature of 75-85° C. for 12-15 hours.

11. A crystalline dolutegravir sodium Form-M4, which has a powder X-ray diffraction pattern having 2Θ angle of significant peaks at about 8.10, 18.40, 19.19, 21.23, 21.72 and 24.02 ±0.2°.

12. A crystalline dolutegravir sodium Form-M4, according to claim 11 which has a powder X-ray diffraction pattern having 2Θ angle of significant peaks at about 6.34, 8.10, 11.82, 12.93, 14.43, 15.63, 16.52, 17.46, 18.40, 19.19, 19.41, 20.09, 21.23, 21.72, 22.27, 24.02, 24.90, 25.65, 27.59, 28.44, 29.70, 30.81, 34.11, 35.54, 38.36 and 46.35±0.2°.

13. A crystalline dolutegravir sodium Form-M4, which has a powder X-ray diffraction pattern as shown in FIG. 3.

14. A process for the preparation of crystalline dolutegravir sodium Form-M4 comprising the step of drying dolutegravir sodium Form-M3 or Form-M2 under reduced pressure at a temperature of 70-140° C. for 15-48 hours.

15. A process for the preparation of crystalline dolutegravir sodium Form-M4 comprising the step of drying dolutegravir sodium Form-M3 or Form-M2 at a temperature of 190-210° C. for 15-20 minutes.

* * * * *